United States Patent [19]

Slepian

[11] Patent Number: 5,634,946

[45] Date of Patent: Jun. 3, 1997

[54] POLYMERIC ENDOLUMINAL PAVING PROCESS

[75] Inventor: Marvin J. Slepian, Tucson, Ariz.

[73] Assignee: Focal, Inc., Lexington, Mass.

[21] Appl. No.: 474,062

[22] Filed: Jun. 7, 1995

Related U.S. Application Data

[60] Division of Ser. No. 118,978, Sep. 9, 1993, abandoned, which is a continuation-in-part of Ser. No. 987,357, Dec. 7, 1992, abandoned, which is a continuation of Ser. No. 857,700, Mar. 25, 1992, Pat. No. 5,213,580, which is a continuation of Ser. No. 593,302, Oct. 3, 1990, abandoned, which is a continuation of Ser. No. 235,998, Aug. 24, 1988, abandoned.

[51] Int. Cl.$^6$ .................................. A61F 2/06; A61F 2/04
[52] U.S. Cl. .................................. 623/11; 623/1; 623/12
[58] Field of Search .................................. 623/1, 11, 12, 623/16; 424/422, 423; 600/36; 604/36, 48, 52, 82, 83, 96; 606/194, 195

[56] References Cited

U.S. PATENT DOCUMENTS

| | | |
|---|---|---|
| 2,642,874 | 6/1953 | Keeling . |
| 2,854,982 | 10/1958 | Pagano . |
| 3,221,745 | 12/1965 | Coover et al. . |

(List continued on next page.)

FOREIGN PATENT DOCUMENTS

| | | |
|---|---|---|
| 0149693 | 7/1985 | European Pat. Off. . |
| 0177330 | 4/1986 | European Pat. Off. . |
| 0183372 | 6/1986 | European Pat. Off. . |
| 0202444 | 11/1986 | European Pat. Off. . |
| 0246638 | 11/1987 | European Pat. Off. . |
| 0248246 | 12/1987 | European Pat. Off. . |
| 0537559A1 | 4/1993 | European Pat. Off. . |
| 0540290A2 | 5/1993 | European Pat. Off. . |
| 0539751A1 | 5/1993 | European Pat. Off. . |
| 2827450 | 1/1979 | Germany . |
| 3640745 | 6/1987 | Germany . |
| WO88/02623 | 4/1988 | WIPO . |
| WO89/12478 | 12/1989 | WIPO . |
| WO90/01969 | 3/1990 | WIPO . |
| WO90/03768 | 4/1990 | WIPO . |
| WO91/01126 | 2/1991 | WIPO . |
| WO91/17731 | 11/1991 | WIPO . |
| WO92/00104 | 1/1992 | WIPO . |
| WO92/00718 | 1/1992 | WIPO . |
| WO92/04393 | 3/1992 | WIPO . |
| WO92/19283 | 11/1992 | WIPO . |
| WO92/21354 | 12/1992 | WIPO . |

OTHER PUBLICATIONS

Peter Barath, M.D. et al., "Combined Angioplasty and Vascular Stenting by a Novel Heat–Expandable Thermoplastic Device" JACC vol. 11, No. 2 — Feb. 1988:65A.

Sandra Blakeslee, "Race is On to Develop Nonsurgical Ways to Unclog Arteries", The New York Times, HEALTH, Jul. 28, 1988.

T. Kerenyi, V. Merjek, Z. Szabolca, A. Pusztai and G. Nadasy, "Local Enzymatic Treatment of Atherosclerotic Plaques", Experimental and Molecular Pathology 49, 330–338 (1988).

McBride et al., "Restenosis After Successful Coronary Angioplasty", The New England Journal of Medicine, Jun. 30, 1988, pp. 1734–1737.

Boretos, J.W. "Improved Intravascular Delivery of Drug Via A Polyethylene Jet Catheter", The 13th Annual Meeting of the Soc. for Biomaterials, Jun. 2–6, 1987, NY.

Derwent Publication Ltd., p. 1, AN 79–04379B, Gould F.E.
Derwent Publications Ltd., p. 1 AN 85–185093.

(List continued on next page.)

*Primary Examiner*—Debra S. Brittingham
*Attorney, Agent, or Firm*—Wolf, Greenfield & Sacks, P.C.

[57] ABSTRACT

A method for applying a paving material to a tissue surface is described. The method involves positioning a non-fluent polymeric material at the surface to be paved, rendering the material fluent, contacting the fluent polymer with the tissue surface, and allowing the polymer to return to its non-fluent condition.

21 Claims, 6 Drawing Sheets

U.S. PATENT DOCUMENTS

| | | |
|---|---|---|
| 3,620,218 | 11/1971 | Schmitt et al. . |
| 3,640,741 | 2/1972 | Etes . |
| 3,707,146 | 12/1972 | Cook et al. . |
| 3,868,956 | 3/1975 | Alfidi et al. . |
| 3,880,158 | 4/1975 | Gurney . |
| 3,987,000 | 10/1976 | Gleichenhagen et al. . |
| 4,023,559 | 5/1977 | Gaskell . |
| 4,080,969 | 3/1978 | Casey et al. . |
| 4,118,470 | 10/1978 | Casey et al. . |
| 4,140,126 | 2/1979 | Choudhury . |
| 4,156,067 | 5/1979 | Gould . |
| 4,200,939 | 5/1980 | Oser ................ 623/16 |
| 4,272,518 | 6/1981 | Moro et al. . |
| 4,286,341 | 9/1981 | Greer et al. . |
| 4,292,299 | 9/1981 | Suzuki et al. . |
| 4,319,363 | 3/1982 | Ketharanathan . |
| 4,377,010 | 3/1983 | Fvdelor et al. . |
| 4,423,725 | 1/1984 | Baran et al. . |
| 4,443,430 | 4/1984 | Mattei et al. . |
| 4,445,892 | 5/1984 | Hussein et al. . |
| 4,448,188 | 5/1984 | Loeb . |
| 4,459,252 | 7/1984 | MacGregor . |
| 4,503,569 | 3/1985 | Dotter . |
| 4,520,823 | 6/1985 | LeVeen et al. . |
| 4,553,545 | 11/1985 | Maass et al. . |
| 4,573,966 | 3/1986 | Weikl et al. . |
| 4,575,373 | 3/1986 | Johnson . |
| 4,578,061 | 3/1986 | Lemelson . |
| 4,580,568 | 4/1986 | Gianturco . |
| 4,588,395 | 5/1986 | Lemelson . |
| 4,595,713 | 6/1986 | St. John . |
| 4,603,695 | 8/1986 | Ikada . |
| 4,610,662 | 9/1986 | Weikl et al. . |
| 4,636,195 | 1/1987 | Wolinsky . |
| 4,643,734 | 2/1987 | Lin . |
| 4,650,466 | 3/1987 | Luther . |
| 4,655,746 | 4/1987 | Daniels et al. . |
| 4,655,771 | 4/1987 | Wallsten . |
| 4,655,777 | 4/1987 | Dunn et al. . |
| 4,674,506 | 6/1987 | Alcond . |
| 4,690,684 | 9/1987 | McGreevy et al. . |
| 4,701,509 | 10/1987 | Sun et al. . |
| 4,702,917 | 10/1987 | Schindler . |
| 4,709,698 | 12/1987 | Johnston et al. . |
| 4,711,777 | 12/1987 | Tan et al. . |
| 4,733,664 | 3/1988 | Kirsch . |
| 4,733,665 | 3/1988 | Palmaz . |
| 4,739,762 | 4/1988 | Palmaz . |
| 4,740,207 | 4/1988 | Kreamer . |
| 4,744,366 | 5/1988 | Jang . |
| 4,754,752 | 7/1988 | Ginsburg et al. . |
| 4,763,538 | 8/1988 | Fujita et al. . |
| 4,763,653 | 8/1988 | Rockey . |
| 4,763,654 | 8/1988 | Jang . |
| 4,771,777 | 9/1988 | Horzewski et al. . |
| 4,776,337 | 10/1988 | Palmaz . |
| 4,776,349 | 10/1988 | Nashef et al. . |
| 4,781,677 | 11/1988 | Wilcox . |
| 4,790,819 | 12/1988 | Li et al. . |
| 4,799,479 | 1/1989 | Spears . |
| 4,820,298 | 4/1989 | Leveen et al. . |
| 4,832,688 | 5/1989 | Sagae et al. . |
| 4,841,968 | 6/1989 | Dunn et al. . |
| 4,853,224 | 8/1989 | Wong . |
| 4,870,966 | 10/1989 | Dellon et al. . |
| 4,900,303 | 2/1990 | Lemelson . |
| 4,923,470 | 5/1990 | Dumican . |
| 4,938,763 | 7/1990 | Dunn et al. . |
| 4,950,735 | 8/1990 | Vanderbilt et al. . |
| 4,969,890 | 11/1990 | Sugita et al. . |
| 5,007,926 | 4/1991 | Derbyshire . |
| 5,015,253 | 5/1991 | MacGregor . |
| 5,037,427 | 8/1991 | Harada et al. . |
| 5,059,211 | 10/1991 | Stack et al. . |
| 5,066,231 | 11/1991 | Oxman et al. . |
| 5,068,220 | 11/1991 | Vanderbilt et al. . |
| 5,077,049 | 12/1991 | Dunn et al. . |
| 5,080,893 | 1/1992 | Goldberg et al. . |
| 5,085,629 | 2/1992 | Goldberg et al. . |
| 5,092,841 | 3/1992 | Spears . |
| 5,100,429 | 3/1992 | Sinofsky et al. . |
| 5,108,416 | 4/1992 | Ryan et al. . |
| 5,124,103 | 6/1992 | Kaplan et al. . |
| 5,126,141 | 6/1992 | Henry . |
| 5,139,480 | 8/1992 | Hickle et al. . |
| 5,145,945 | 9/1992 | Tang et al. . |
| 5,147,385 | 9/1992 | Beck et al. . |
| 5,158,548 | 10/1992 | Lau et al. . |
| 5,175,000 | 12/1992 | Godowski et al. . |
| 5,181,903 | 1/1993 | Vann et al. . |
| 5,190,540 | 3/1993 | Lee . |
| 5,192,307 | 3/1993 | Wall . |
| 5,199,951 | 4/1993 | Spears . |
| 5,213,580 | 5/1993 | Slepian et al. . |
| 5,232,444 | 8/1993 | Just et al. . |
| 5,242,399 | 9/1993 | Lau et al. . |
| 5,278,201 | 1/1994 | Dunn et al. . |
| 5,278,202 | 1/1994 | Dunn et al. . |
| 5,292,321 | 3/1994 | Lee . |
| 5,300,020 | 4/1994 | L'Esperance, Jr. . |
| 5,306,286 | 4/1994 | Stack et al. . |
| 5,324,519 | 6/1994 | Dunn et al. . |
| 5,324,520 | 6/1994 | Dunn et al. . |
| 5,340,849 | 8/1994 | Dunn et al. . |
| 5,368,859 | 11/1994 | Dunn et al. . |
| 5,395,615 | 3/1995 | Godowski et al. . |
| 5,397,307 | 3/1995 | Goodin . |

OTHER PUBLICATIONS

Palmaz, et al., Normal and Stenotic Renal Arteries: Experimental Balloon–Expandable Intraluminal Stenting, Radiology; 164: 705–708 (1987).

Poppas, D.P. et al., "Laser Welding in Urethral Surgery; Improved Results with a Protein Solder", The Journal of Urology, vol. 139, Feb., 1988, pp. 415–417.

Slepian, Marvin J., "Polymeric Endoluminal Paving and Sealing: Therapeutics at the Crossroad of Biomechanics and Pharmacology", Interventional Cardiology (Textbook), Ch. 32: Ed. E.J. Topol, Saunders, Philadelphia (1990).

Boretos, John W. et al., "Segmented Polyurethane: A Polyether Polymer An Initial Evaluation for Biomedical Applications", J. Biomed Mater. Res., vol. 2, pp. 121–130 (1968).

POLYMERIC ENDOLUMINAL PAVING PROCESS

This application is a division of copending application Ser. No. 08/118,978, filed Sep. 9, 1993, abandoned, which is a continuation-in-part of Ser. No. 07/987,357, filed Dec. 7, 1992, abandoned, which is a continuation of Ser. No. 07/857,700, filed Mar. 25, 1992, issued as U.S. Pat. No. 5,213,580, which is a file wrapper continuation of Ser. No. 07/593,302, filed Oct. 3, 1990, abandoned, which is a file wrapper continuation of Ser. No. 07/235,998, filed Aug. 24, 1988, abandoned.

BACKGROUND OF THE INVENTION

This invention relates to a novel method for the in vivo paving of the interior of organs or organ components and other tissue cavities, and to apparatus and polymeric products for use in this method. The tissues involved may be those organs or structures having hollow or tubular geometry, for example blood vessels such as arteries or veins, in which case the polymeric products are deposited within the naturally occurring lumen. Alternatively, the tissue may be a normally solid organ in which a cavity has been created either as a result of a surgical procedure, a percutaneous intervention, an accidental trauma, or disease.

The hollow or tubular geometry of organs commonly has functional significance such as in the facilitation of fluid or gas transport (blood, urine, lymph, oxygen or respiratory gasses) or cellular containment (ova, sperm). Disease processes may affect organ tissue or its components by encroaching upon, obstructing or otherwise reducing the cross-sectional area of the hollow or tubular elements. Additionally, other disease processes may violate the native boundaries of the hollow organ and thereby affect its barrier function and/or containment ability. The ability of the organ or structure to properly function can then be severely compromised. A good example of this phenomena can be seen in the coronary arteries.

Coronary arteries, or arteries of the heart, perfuse the cardiac muscle with arterial blood. They also provide essential nutrients, removal of metabolic wastes, and gas exchange. These arteries are subject to relentless service demands for continuous blood flow throughout the life of the patient.

Despite their critical life supporting function, coronary arteries are often subject to attack through several disease processes, the most notable being atherosclerosis (hardening of the arteries). Throughout the life of the patient, multiple factors contribute to the development of microscopic and/or macroscopic vascular lesions known as plaques.

The development of a plaque-lined vessel typically leads to an irregular inner vascular surface with a corresponding reduction of lumen cross-sectional area. The progressive reduction in cross-sectional area compromises flow through the vessel. In the case of the coronary arteries, the result is a reduction in blood flow to the cardiac muscle. This reduction in blood flow, coupled with a corresponding reduction in nutrient and oxygen supply, often results in clinical angina, unstable angina, myocardial infarction (heart attack), and death. The clinical consequences of the above process and its overall importance are evidenced by the fact that atherosclerotic coronary artery disease represents the leading cause of death in the United States today.

Historically, for coronary artery disease states beyond those which can be treated solely with medication, the treatment of advanced atherosclerotic coronary artery disease involved cardio-thoracic surgery in the form of coronary artery bypass grafting (CABG). In that procedure, the patient is placed on cardio-pulmonary bypass and the heart muscle is temporarily stopped. Repairs are then surgically affected on the heart in the form of detour conduit grafted vessels to provide blood flow around obstructions. While CABG has proven to be quite effective, it carries with it inherent surgical risks and requires a lengthy, often painful recuperation period. In the United States alone approximately 150,000-200,000 people are subjected to open heart surgery annually.

In 1977 a major advance in the treatment of atherosclerotic coronary artery disease occurred with the introduction of a technique known as Percutaneous Transluminal Coronary Angioplasty (PTCA). PTCA involves the retrograde introduction, typically from an artery in the arm or leg to the area of vessel occlusion, of a catheter with a small dilating balloon at its tip. The catheter is guided through the arteries via direct fluoroscopic guidance and passed across the luminal narrowing of the vessel. Once in place, the catheter balloon is inflated to several atmospheres of pressure. This results in "cracking", "plastic" or other mechanical deformation of the lesion or vessel with a subsequent increase in the cross-sectional area through the lesion. This in turn reduces obstruction and trans-lesional pressure gradients and increases blood flow.

PTCA is an extremely effective treatment with a relatively low morbidity. The procedure has rapidly become the primary therapy in the treatment of advanced atherosclerotic coronary disease throughout the United States and the world. By way of example, since its introduction in 1977, the number of PTCA cases now exceeds 300,000 per annum in the United States and in 1987, for the first time surpassed the number of bypass operations performed. Moreover, as a result of PTCA, emergency coronary artery bypass surgery is required in less than four percent of patients.

Typically, atherosclerosis is a diffuse arterial disease process exhibiting simultaneous patchy involvement in several coronary arteries. Patients with this type of widespread coronary involvement, while previously not considered candidates for angioplasty, are now being treated due to technical advances and increased clinical experience.

Despite the major therapeutic advance in the treatment of coronary artery disease which PTCA represents, its success has been hampered by the development of vessel renarrowing or reclosure following dilation. During a period of hours or days post procedure, significant total vessel reclosure may develop in up to 10% of cases. This occurrence is referred to as "abrupt reclosure". However, the more common and major limitation of PTCA, is the development of progressive reversion of the vessel to its closed condition, negating any gains achieved from the procedure.

This more gradual renarrowing process is referred to as "restenosis" Post-PTCA follow-up studies report a 10-50% incidence (averaging approximately 30%) of restenosis in cases of initially successful angioplasty. Studies of the time course of restenosis have shown that it is typically an early phenomenon, occurring almost exclusively within the six months following an angioplasty procedure. Beyond this six-month period, the incidence of restenosis is quite rare. Despite recent pharmacologic and procedural advances, little success has been achieved in preventing either abrupt reclosure or restenosis post-angioplasty.

Restenosis has become even more significant with the increasing use of multi-vessel PTCA to treat complex coronary artery disease. Studies of restenosis in cases of multi-vessel PTCA reveal that after multi-lesion dilatation, the risk of developing at least one recurrent coronary lesion ranges from about 26% to 54% and appears to be greater than that reported for single vessel PTCA. Moreover, the incidence of restenosis increases in parallel with the severity of the pre-angioplasty vessel narrowing. This is significant in light of the growing use of PTCA to treat increasingly complex multi-vessel coronary artery disease.

The 30% overall average restenosis rate has significant costs including patient morbidity and risks as well as medical economic costs in terms of follow-up medical care, repeat hospitalization and recurrent catherization and angioplasty procedures. Most significantly, prior to recent developments, recurrent restenosis following multiple repeat angioplasty attempts could only be rectified through cardiac surgery with the inherent risks noted above.

In 1987, a mechanical approach to human coronary artery restenosis was introduced. That approach is commonly referred to as "Intracoronary Stenting". One type of intracoronary stent is a tubular device made of fine wire mesh, typically stainless steel. A stent of that type is disclosed in U.S. Pat. No. 4,655,771. The device can be radially compressed so as to be of low cross-sectional area. In this "low profile" condition, the mesh is placed in or on a catheter similar to those used for PTCA. The stent is then positioned at the site of the vascular region to be treated. Once in position, the wire mesh stent is released and allowed to expand to its desired cross-sectional area generally corresponding to the internal diameter of the vessel. Similar solid stents are also disclosed in U.S. Pat. No. 3,868,956 to Alfidi et al.

The metal stent functions as a permanent intra-vascular scaffold. By virtue of its material properties, the metal stent provides structural stability and direct mechanical support to the vascular wall. Stents of the type described above are resiliently self-expanding due to their helical "spring" geometry. Recently, slotted steel tubes and extended spring designs have been introduced. These are deployed through application of direct radial mechanical pressure conveyed by a balloon or other radial expansion device at the catheter tip. Such a device and procedure are disclosed in U.S. Pat. No. 4,733,665 to Palmaz. Despite certain significant limitations and potentially serious complications (discussed below), this type of stent has been successful with an almost 100% acute patency rate and a marked reduction in the restenosis rate.

Other stents have also been designed in recent years. Among these are stents formed from polymeric materials and stents formed from materials which exhibit shape memory. In the latter case, stents formed from the shape memory alloy Nitinol have been disclosed in the prior art.

The complications associated with permanent implants such as the Palmaz device result from both the choice of material, as well as the inherent design deficiencies in the stenting devices. The major limitation lies in the permanent placement of a non-retrivable, non-degradable, foreign body in a vessel to combat restenosis which is predominately limited to the six-month time period post-angioplasty. There are inherent, significant risks common to all permanent implant devices. Moreover, recent studies have revealed that atrophy of the media, the middle arterial layer of a vessel, may occur as a specific complication associated with metal or other permanent stenting due to the application of continuous lateral expansile forces after implantation.

These problems are even more acute in the placement of a permanent metallic foreign body in the vasculature associated with the cardiac muscle. Coronary arteries are subjected to extreme service demands requiring continuous unobstructed patency with unimpeded flow throughout the life of the patient. Failure in this system can lead to myocardial infarction (heart attack) and death. In addition, torsional and other multi-directional stresses encountered in and near the heart, due to its continuous oscillatory/cyclic motion, further amplify the risks associated with permanent, stiff intra-arterial implants in the coronary region.

It has been observed that, on occasion, recurrent intra-vascular narrowing has occurred following stent placement in vessels during a period of several weeks to months. Typically, this occurs "peri-stent", i.e., immediately upstream or downstream from the stent. It has been suggested that this may relate to the often significantly different compliances of the vessel and the stent, sometimes referred to as "compliance mismatch". Aside from changes in compliance, another important mechanism leading to luminal narrowing above and below the stent may be the changes in shear forces and fluid flows encountered across the sharp transitions of the stent-vessel interface. Further supporting evidence has resulted from studies of vascular grafts which reveal a higher incidence of thrombosis and eventual luminal closure also associated with significant compliance mismatch.

To date, known stent designs, (i.e., tubular, wire helical or spring, and scaffold) have been designed with little consideration or measurement of their radial stiffness. Recent studies measuring the relative radial compressive stiffness of known wire stents, as compared to physiologically pressurized arteries, have found the stents to be much stiffer than biological tissue. These studies lend support to the concept of poor mechanical biocompatibility of currently available stents.

Conventional metal stenting is also limited since it requires the availability of numerous stents of differing sizes (as well as associated deployment devices) to accommodate treatment of blood vessels of differing sizes. Additionally metal stents provide a relatively rigid nonflexible structural support which is not amenable to a wide variety of endoluminal geometries, complex surfaces, luminal bends, curves or bifurcations.

The identified risks and limitations of metal and non-metal permanent stents have severely limited their utility in coronary artery applications. Thus, a need exists for stents which are non-permanent and have a compliance that more closely matches that of blood vessels. A need also exists for stents which may be tailored in length and radial diameter to properly match a wide variety of treatment sites. A need also exists for methods for providing polymeric materials to various body lumens and hollow spaces, whether occurring naturally or as a result of surgery, trauma or disease.

SUMMARY OF THE INVENTION

The present invention provides an alternative to conventional stenting techniques as well as a method for providing biocompatible polymeric materials in vivo. The invention relates to a novel method for polymeric endoluminal paving and sealing (PEPS) which involves application of a polymeric material to the interior surface of a blood vessel, tissue lumen or other hollow space. The material may also be applied to tissue contacting surfaces of implantable medical devices. In accordance with this method, a polymeric material, either in the form of a monomer or prepolymer solution or in the form of an at least partially pre-formed polymeric product, is introduced into the lumen or hollow space and positioned at an area to be treated. The polymeric product is then reconfigured to conform to and maintain intimate contact with the interior surface of the lumen or hollow such that a paving and sealing coating is achieved.

In general, the present invention relates to a method for forming a biocompatible polymer coating on a tissue surface by providing a biocompatible polymeric material that is non-fluent at body temperature, yet which becomes fluent at an elevated temperature. The material is heated to render it fluent, contacted with a tissue surface to be coated, and allowed to cool, thereby providing a non-fluent biocompatible polymeric coating on the tissue surface. In connection with the step of contacting the polymeric material with the tissue surface, the fluent polymeric material may be molded to provide a coating having desired surface or shape characteristics. The transition of the polymer from a non-fluent state to a fluent state and vice versa may be the result of a phase change in which the polymeric material goes from a solid to a liquid state, or in the alternative, it may be the result of a viscosity change with the polymeric material remaining in a single phase throughout.

Although having particular advantages for preventing restenosis in coronary blood vessels following angioplasty, the PEPS approach is not limited to use in connection with restenosis. The procedure can also be effectively employed in any tubular or hollow organ to provide local structural support, smooth surface characteristics, improved flow, barrier placement or imposition, and sealing of lesions. In addition, the polymeric paving and sealing material may incorporate therapeutic agents such as drugs, drug producing cells, cell inhibition and/or regeneration factors or even progenitor cells of the same type as the involved organ or a histologically different organ to accelerate and/or inhibit or retard healing processes. Materials with incorporated therapeutic agents may be effectively used to coat or plug hollow spaces or lumens formed by surgery, trauma or disease in normally solid organs as well as to coat or plug hollow spaces or lumens formed by surgery, percutaneous techniques, trauma or disease in normally hollow or tubular organs.

The present invention also relates to the use of at least partially preformed polymeric products. These products may have any of a variety of physical shapes and sizes in accordance with the particular application. The invention also provides apparatus specially adapted for the positioning of the polymeric material, these including partially preformed polymeric products, at the interior surface of an organ and for the subsequent chemical or physical reconfiguration of the polymeric material such that it assumes a desired molded or customized final configuration.

DETAILED DESCRIPTION OF THE INVENTION

In general, PEPS involves the introduction of a polymeric material onto a selected location on a tissue surface or a tissue-contacting surface of an implantable medical device. The tissue surface may be an internal or external surface, and can include the interior of a tissue lumen or hollow space whether naturally occurring or occurring as a result of surgery, percutaneous techniques, trauma or disease. The polymeric material is then reconfigured to form a coating or "paving" layer in intimate and conforming contact with the interior surface. The resulting paving layer optionally can have a sealing function. As used herein, the term "sealing" or "seal" means a coating of sufficiently low porosity that the coating provides a barrier function. The term "paving" refers to coatings in general wherein the coatings are porous or perforated or are of a low porosity "sealing" variety. The coating preferably has a thickness on the tissue surface on the order of 0.001–1.0 mm, however, coatings having a thickness outside that range may be used as well. By appropriate selection of the polymeric material employed and of the configuration of the paving material, PEPS provides a unique customizable process, which can be tailored to satisfy a wide variety of biological or clinical situations.

Broadly, the polymeric material comprises a biocompatible polymeric material having a variable degree of fluency in response to a stimulus. Thus, the material may be such that it is substantially non-fluent in vivo. The material can be positioned adjacent to a tissue or non-tissue surface to be coated and then stimulated to render it fluent. The fluent polymeric material is contacted with the surface to be paved, and the polymer is then allowed to return to its non-fluent state, thereby providing a coating in the form of a biocompatible polymeric paving on the surface.

Generally, the paving process is carried out by providing a biocompatible polymeric material that is non-fluent at body temperature, yet which may be rendered fluent at an elevated temperature. The material is positioned at either an internal or external treatment location and then heated to render the polymeric material fluent. The fluent polymeric material is contacted with the tissue surface to be paved or sealed, and the polymer is then allowed to cool into a non-fluent coating in the form of a biocompatible polymeric paving on the tissue surface.

During the step of positioning the material at the desired location, the location may be accessed by either invasive surgical techniques or by relatively non-invasive techniques such as laparoscopic procedures or percutaneous transluminal procedures. In one embodiment, the step in which the fluent polymeric material is contacted with the tissue surface may be considered as a "molding" procedure in which the fluent polymeric material is molded into substantially conforming contact with the body tissue before cooling into a non-fluent coating on the surface. It is noted that the transition of the material from a non-fluent to a fluent state, and vice-versa, may involve a phase change in the material, however, such a phase change is not necessary. For example, in certain embodiments, the terms "non-fluent" and "fluent" are primarily relative descriptions of a material which undergoes a significant change in viscosity and flowability without undergoing an actual phase change. Alternatively, the transition of the material between its fluent and non-fluent states may be the result of an actual phase change in the material resulting either from the addition or removal of energy from the material.

The basic requirements for the polymeric material to be used in the PEPS process are biocompatibility and the capacity to be chemically or physically reconfigured under conditions which can be achieved in vivo. Such reconfiguration conditions may involve heating, cooling, mechanical deformation, (e.g., stretching), or chemical reactions such as polymerization or crosslinking.

Suitable polymeric materials for use in the invention include both biodegradable and biostable polymers and copolymers of carboxylic acids such as glycolic acid and lactic acid, polyalkylsulfones, polycarbonate polymers and copolymers, polyhydroxybutyrates, polyhydroxyvalerates and their copolymers, polyurethanes, polyesters such as poly(ethylene terephthalate), polyamides such as nylons, polyacrylonitriles, polyphosphazenes, polylactones such as polycaprolactone, polyanhydrides such as poly[bis(p-carboxyphenoxy)propane anhydride] and other polymers or copolymers such as polyethylenes, hydrocarbon copolymers, polypropylenes, polyvinylchlorides and ethylene vinyl acetates.

The paving material is preferably a homopolymer, or a binary or teriary copolymer, however, copolymers having more than three constituents are intended to be included as well.

The polymers and copolymers may sometimes contain additives such as plasticizers (e.g., citrate esters), to improve their function, such as to reduce the temperature at which sufficient fluency is obtained. In addition, physical blends of polymers including the combinations of several different biostable and/or biodegradable polymers could be utilized in this process. Likewise the process allows polymeric composites or blends of the polymers described above incorporating separate polymeric, metallic, or other material domains to be introduced onto tissue or tissue contacting surfaces. Such domains may be present as randomly or uniformly distributed microparticles, microcapsules, nanoparticles, nanocapuless or liposomes of uniform or random size shape or compositions.

Other bioabsorbable polymers could also be used either singly or in combination. For example, homopolymers and copolymers of delta-valerolactone and p-dioxanone as well as their copolymers can be crosslinked with bis-caprolactone to provide material for use in PEPS. Likewise, copolymers of polycaprolactones and lactides are also considered to be particularly useful in the present invention.

In one embodiment, PEPS utilizes biodegradable polymers, with specific degradation characteristics to provide material having a sufficient lifespan for the particular application. As used herein, "biodegradable" is intended to describe polymers and copolymers that are non-permanent and removed by natural or imposed therapeutic biological and/or chemical processes. As such, bioerodable or bioabsorbable polymers and the like are intended to be included within the scope of that term. As noted above, a six month lifespan is probably sufficient for use in preventing restenosis. Shorter or longer periods, or permanent biostable materials may be appropriate for other therapeutic applications.

The polycaprolactones disclosed in U.S. Pat. No. 4,702,917 to Schindler, incorporated herein by reference, are highly suitable bioabsorbable polymers for use in the PEPS process, particularly for prevention of restenosis. Polycaprolactones possess adequate mechanical strength being mostly crystalline even under quenching conditions. Despite their structural stability, polycaprolactones are much less rigid than the metals used in traditional stenting, thereby minimizing the risk of acute vessel wall damage from sharp or rough edges. In the case of a polycaprolactone, for example, the crystalline structure of the polymer will maintain a constant outside diameter. This eliminates risks often associated with known helical or spring metal stents which, after being expanded in vivo, have a tendency to exert continuous pressure on the vessel wall.

The rate of bioabsorption of polycaprolactone is ideal for the applications of the invention. The degradation process of this polymer has been well characterized with the primary degradation product being nontoxic 6-hydroxy hexanoic acid of low acidity. Furthermore, the time over which biodegradation of polycaprolactone occurs can be adjusted through copolymerization.

Polycaprolactone has a crystalline melting point of 60° C. and can be deployed in vivo via a myriad of techniques which facilitate transient heating and varying degrees of mechanical deformation or application as dictated by individual situations. This differs markedly from other bioabsorbable polymers such as polyglycolide and polylactide which melt at much higher temperatures (approximately 180° C.) thereby raising the possiblility of deleterious tissue exposure due to excessive temperatures.

Polyanhydrides have been described for use as drug carrier matrices by Leong et al., J. Biomed. Mat. Res. 19, 941–955 (1985). These materials frequently have fairly low glass transition temperatures, in some cases near normal body temperature, which makes them mechanically deformable with only a minimum of localized heating. Furthermore, they offer erosion times varying from several months to several years depending on particular polymer selected.

Heating of the polymeric material to render it fluent may be achieved using a variety of methods. For example, the polymer may be heated using a heated fluid such as hot water or saline, or it may be heated using radiofrequency energy or resistance heating. Alternatively, the polymer may be heated using light such as light having a wavelength in the infrared, visible, or ultraviolet spectrum. In still other embodiments, heating may be achieved using microwaves or radiation produced by fission or fusion processes.

The polymeric materials may be applied in custom designs, with varying thicknesses, lengths, and threedimensional geometries (e.g. spot, stellate, linear, cylindrical, arcuate, spiral) to achieve varying finished geometries as depicted in FIGS. 1–8. Further, PEPS may be used to apply polymer to the inner surfaces of hollow, cavernous, or tubular biological structures (whether natural or artificially formed) in either single or multiple polymer layer configurations. PEPS may also be used, where appropriate, to occlude a tissue lumen completely.

Further to the above, the paving coating may be applied as a continuous layer either with or without perforations. As noted earlier, in the case in which the paving coating is applied without perforations, it is referred to as a to act as a barrier layer on the surface of the tissue. Such coatings may also be used to provide structural support to the tissue, locally deliver therapeutic agents to the tissue surface, or achieve any of the other therapeutic effects, either alone or in combination, described herein. Although porous or perforated paving layers do not provide a barrier effect, each of the other aspects of the material described herein may be achieved. It is noted that as used herein the term "continuous" refers to coatings interconnected as a single unit as opposed to "discontinuous" layers which are formed of a plurality of isolated, discontinuous domains of the coating material.

The polymeric materials used in PEPS can be combined with a variety of therapeutic agents for on-site delivery. Examples of such materials for use in coronary artery applications are anti-thrombotic agents, e.g., prostacyclin, heparin and salicylates, thrombolytic agents e.g. streptokinase, urokinase, tissue plasminogen activator (TPA) and anisoylated plasminogen-streptokinase activator complex (APSAC), vasodilating agents i.e. nitrates, calcium channel blocking drugs, anti-proliferative agents i.e. colchicine and alkylating agents, intercalating agents, antisense oligonucleotides, ribozymes, aptomers, growth modulating factors such as interleukins, transformation growth factor β and congeners of platelet derived growth factor, monoclonal antibodies directed against growth factors, anti-inflammatory agents, both steriodal and non-steroidal, modified extracellular matrix components or their receptors, lipid and cholesterol sequestrants and other agents which may modulate vessel tone, function, arteriosclerosis, and the healing response to vessel or organ injury post intervention. In applications where multiple polymer layers are used, different pharmacological agents could be used in different polymer layers. Moreover, PEPS may be used to effect pharmaceutical delivery focally within the vessel wall, i.e. media. It is noted that delivery of therapeutic agents is not limited to coronary artery applications. Rather, any tissue surface that may benefit from the local application of therapeutic agents is contemplated as a site for treatment using the methods and apparatus for the present invention.

The polymeric material in accordance with the invention may also have incorporated in it living cells (whether naturally occurring or produced through recombinant DNA technology), artificial cells, cell ghost (i.e., RBC or platelet ghosts), liposomes, or pseudoviriones, to serve any of several purposes. For example, the cells may be selected to produce specific agents such as growth factors at the local tissue location. In such a way, a continuously regenerating supply of a therapeutic agent may be provided without concerns for stability, initial overdosing and the like.

Cells incorporated in the polymeric material may also be progenitor cells corresponding to the type of tissue at the treatment location or other cells providing therapeutic advantages. For example, liver cells might be incorporated into the polymeric material and implanted in a lumen created in the liver of a patient to facilitate regeneration and closure of that lumen. This might be an appropriate therapy in cases where disease (e.g. cirrhosis, fibrosis, cystic disease or malignancy) results in non-functional tissue, scar formation or tissue replacement with cancerous cells. Similar methods may be applied to other organs as well. The process of carrying out such treatment involves first inserting a catheter into a lumen within a diseased organ segment. The lumen can be a native vessel or it can be a man-made lumen, for example, a cavity produced by a laser. A polymeric plug is introduced into the lumen. The catheter is then removed, leaving the plug in place to act as a focus for new growth stemming from cells implanted along with the polymeric plug. If the desire is for a more tubular structure, the plug can be appropriately reconfigured.

Optional additions to the polymeric material such as barium, iodine or tantalum salts for X-ray radio-opacity allow visualization and monitoring of the coating.

The technique of PEPS preferably involves the percutaneous application of a polymeric material, for example, a biodegradable polymer such as polycaprolactone, either alone or mixed with other biodegradable polymeric materials. As noted above, the polymeric material may optionally contain various pharmaceutical or therapeutic agents for controlled sustained release at the treatment location. The polymeric material is typically applied to an organ surface using both thermal and mechanical means to manipulate the polymeric material. Although capable of being used during conventional surgery, PEPS will generally be applied using minimally invasive surgical techniques. The coating typically will be applied using some type of catheter, such as a modified PTCA catheter. PEPS is preferably applied using a single catheter with single or multiple balloons and lumens. The catheter should be of relatively low cross-sectional area. A long thin tubular catheter manipulated using fluoroscopic guidance is preferred for providing access to the interior of organ or vascular areas.

The polymer may be deployed in the interior of the vessel or organ from the surface or tip of the catheter. Alternatively, the polymer could be positioned on a balloon such as that of a standard angioplasty balloon catheter. Additionally, the polymer could be applied by spraying, extruding or otherwise internally delivering the polymer via a long flexible tubular device having multiple lumens.

The polymeric material may take the form of a sleeve designed to be readily insertable along with the catheter into the tissue lumen, and then to be deployed onto the wall of the lumen to form the coating. This deployment can be accomplished by positioning a polymeric preform over the balloon portion of a dilatation catheter, and partially inflating the balloon to hold the preform in position. Upon guiding the preform to a desired treatment site, the preform is rendered fluent using, for example, heated saline. The balloon is then fully inflated, which expands the fluent polymeric preform, causing it is press against the walls of the tissue lumen and acquire a shape corresponding to the lumen wall. This shape is then fixed, upon cooling of the preform to a non-fluent state, and the catheter is removed leaving behind a polymeric paving or seal on the lumen wall.

The process of fixing the shape of the polymeric material can be accomplished in several ways, depending on the character of the original polymeric material. For example, a partially polymerized material can be expanded using the balloon after which the conditions are adjusted such that polymerization can be completed, e.g., by increasing the local temperature or providing infrared, visible, or UV radiation through an optical fiber. A temperature increase might also be used to soften a fully polymerized sleeve to allow expansion and facilitate reconfiguration and local molding, after which it would "freeze" in the expanded position when the heat source is removed. If the polymeric sleeve is a plastic material which will permanently deform upon stretching (e.g., polyethylene, nylon or polyvinyl chloride), no special fixation procedure is required.

Local heating can be provided by a flow of heated liquid directly into the tissue lumen. Thermal control can also be provided, however, using a fluid flow through or into the balloon, or using a partially perforated balloon such that temperature control fluid passes through the balloon into the lumen. Thermal control can also be provided using electrical resistance heating via a wire running along the length of the catheter body in contact with resistive heating elements. This type of heating element can make use of DC or radio frequency (RF) current or external RF or microwave radiation. Other methods of achieving temperature control can also be used, including light-induced heating using an internal optical fiber (naked or lensed).

Variations in the ultimate configuration of the PEPS coating can also be achieved by using more complex deployments of the polymer on the expansile number. For example, the polymer can be in the form of a perforated tubular sleeve, a helical sleeve or a plurality of discontinuous members of various shapes. These may be affixed to the expansile member-directly, for example with an adhesive, or by suction through perforations and the like, or the affixation can be achieved using an overcoating such as dissolvable gauze-like or paper sheath (i.e. spun saccharide). Alternatively, the polymer can be held in place by a retractable or porous sheath which will be removed with the catheter after application.

Application of the polymeric material may be accomplished by extruding a solution of monomers or prepolymers through a catheter to coat or fill a tissue lumen or hollow space. The formation of a polymer coating can be controlled by introducing crosslinking agents or polymerization catalysts together with the monomer or prepolymer solution and then altering the conditions such that polymerization occurs. Thus, when a balloon catheter is used, a flow of heated fluid into the balloon can increase the local temperature to a level sufficient to induce or accelerate polymerization. Alternatively, the monomer/prepolymer solution might be introduced cold, with metabolic temperature being sufficient to induce polymerization.

Catheter bodies for use in this invention can be made of any known material, including metals, e.g. steel, and thermoplastic polymers. Occluding balloons may be made from compliant materials such as latex or silicone, or non-compliant materials such as polyethylene terephthalate (PET). The expansile member is preferably made from non-compliant materials such as PET, PVC, polyethylene or nylon. If used, the balloon catheter portion of a dilatation may optionally be coated with materials such as silicones, polytetrafluoroethylene (PTFE), hydrophilic materials like hydrated hydrogels and other lubricious materials to aid in separation of the polymer coating.

In addition to arteries, the PEPS process may be utilized for other applications such as paving the interior of veins, ureters, urethras, bronchi, biliary and pancreatic duct systems, the gut, nasolacrimal ducts, sinus cavities, the eye, and eustachian, spermatic and fallopian tubes. Likewise the process may be used to provide a paving layer in the context of transhepatic portosystemic shunting, dialysis grafts, arterio-venous fistulae, and aortic and other arterial aneurysms. The paving and sealing material of the PEPS process can also be used in other direct clinical applications even at the coronary level. These include but are not limited to the treatment of abrupt vessel reclosure post PCTA, the "patching" of significant vessel dissection, the sealing of vessel wall "flaps" either secondary to catheter injury or spontaneously occurring, or the sealing of aneurysmal coronary dilations associated with various arteritidies. Further, PEPS provides intraoperative uses such as sealing of vessel anastomoses during coronary artery bypass grafting and the ability to provide a "bandaged" smooth polymer surface.

The unique pharmaceutical delivery function of the PEPS process may be readily combined with "customizable" deployment geometry capabilities to accommodate the interior of a myriad of complex organ or vessel surfaces. Most importantly, this customized geometry can be made from structurally stable yet biodegradable polymers. The ability to tailor the external shape of the deployed polymer through melted polymer flow into uneven surface interstices, while maintaining a smooth interior surface with good flow characteristics, will facilitate better structural support for a variety of applications including eccentric coronary lesions which by virtue of their geometry are not well bridged with conventional metal stents.

As noted above, a polymer substrate used in PEPS may be fashioned out of extruded tubes of polycaprolactone or copolymers containing polycaprolactone. The initial predeployment design and size of the polymer sleeve will be dictated by the specific application based upon the final deployed physical, physiological and pharmacological properties desired. In an alternative embodiment, the polymeric material may be provided in the form of a rolled sheet of material which is radially expanded and pressed into contact with a tissue surface by an unrolling procedure. The material of the rolled sheet may be rendered fluent prior to, during, or following the unrolling procedure.

For coronary artery application, predeployment tubes of about 10 to 20 mm in length and about 1 to 2 mm in diameter may be used. The initial wall thickness of the resulting in vivo polymer layer may be varied depending upon the nature of the particular application. In general, coating procedures require polymer layers of about 0.001 to 1.0 mm while layers which are designed to give structural support can vary from 0.05 mm to 5.0 mm.

The polymer tube walls may be processed prior to insertion with either light-induced or chemical etching, pitting, slitting or peforation depending upon the application. In addition, the shape of any micro (10 nm to 1 $\mu$m) or macro (>1 $\mu$m to 4.0 mm) perforation may be further geometrically modified to provide various surface areas on the inner versus outer seal surface. The surfaces of the predeployed polymer may be further modified with bound, coated, or otherwise applied agents, i.e., cyanoacrylates or biological adhesives such as those derived from fungal spores, sea mussel or autologous fibrinogen adhesive derived from blood.

For PEPS applications involving the coronary arteries, the polymer tubes (if in an initial tubular configuration), may include perforations or pores. This will ensure a symmetric expansion of the encasing polymeric sealant. By using a fragmented tubular polymer surface with corresponding expansions along predicted perforations, a significant mechanical stability is provided. In addition, the amount of foreign material placed within the vessel would be minimized.

Depending upon the polymer and pharmaceutical combination and the configuration, PEPS may be used to coat or bandage the inner surface of an organ with a thin adhesive partitioning polymer film or layer of about 0.005 mm to 1.0 mm. Biodegradable polymers thus applied to an internal organ or vessel surface will act as an adherent film "bandage". This improved surface, with desirable rheologic and adherence properties, facilitates improved fluid or gas transport in and through the body or lumen of the vessel or hollow organ structure and acts to reinstate violated native surfaces and boundaries.

The ultimate in vivo deployed geometry of the polymer dictates the final function of the polymer coating. The thinner applications allow the polymer film to function as a coating, sealant, partitioning barrier, bandage, and/or drug depot. Complex internal applications of thicker layers of polymer, such as intravessel or intra-luminal applications can provide increased structural support, and can serve a mechanical role to maintain vessel or organ patency.

For example, lesions which are comprised mostly of fibromuscular components have a high degree of viscoelastic recoil. These lesions would require using the PEPS process to apply an intraluminal coating of greater thickness and extent so as to impart more structural stability thereby resisting vessel radial compressive forces. The PEPS process in this way provides structural stability and is generally applicable for the maintenance of the intraluminal geometry of tubular biological organs or substructures. It may be used in this way following the therapeutic return of normal architecture associated with balloon dilation (PTCA), atherectomy, or any recanalization procedures, however, the use is not intended to be limited as such.

An important feature of the PEPS technique is the ability to customize the application of the polymer to the internal surface of a vessel or organ as dictated by the particular application. This results in a variety of possible geometries of polymer as well as a variety of forms. These multi-geometry, multi-form polymer structures may be adjusted to correspond to particular functions. (FIGS. 1–8)

Figure 1:
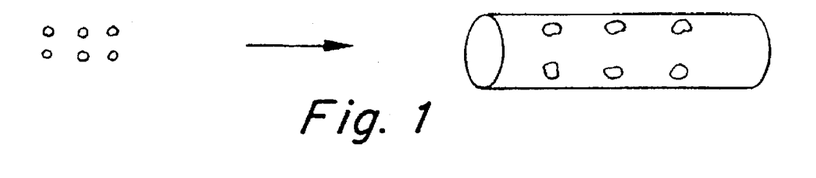
FIG. 1 shows an amorphous geometry of the PEPS polymer coating before and after deployment.
Figure 2:
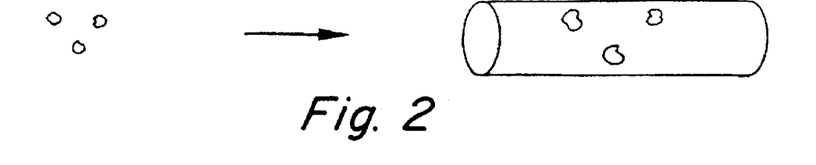
FIG. 2 shows a stellate geometry of the PEPS polymer coating before and after deployment.
Figure 6:
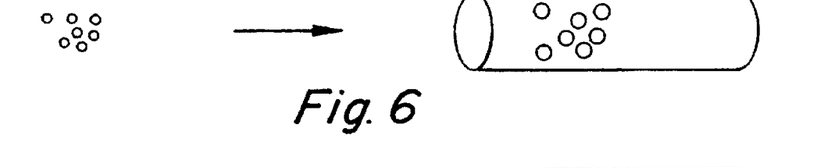
FIG. 6 shows a spot geometry of the PEPS process before and after deployment.
Figure 7:
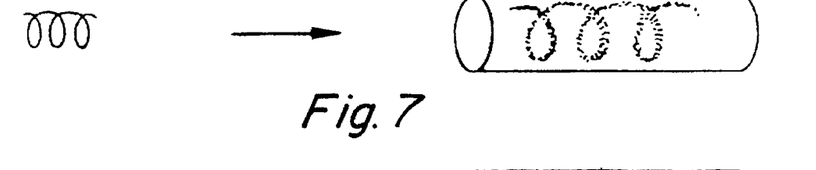
FIG. 7 shows a spiral form application of the PEPS process before and after deployment.

With particular reference to FIGS. 1–8 the PEPS process may be effectuated so that the focal application of polymer to the vessel or organ results in either an amorphous geometry, FIG. 1, stellate geometry, FIG. 2, or spot geometry, FIG. 6.

Figure 3:
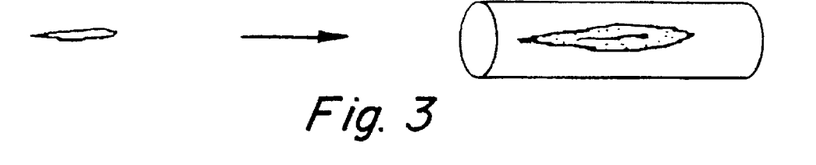
FIG. 3 shows a linear feathered polymer strip applied to "one" wall before and after deployment.
Figure 4:
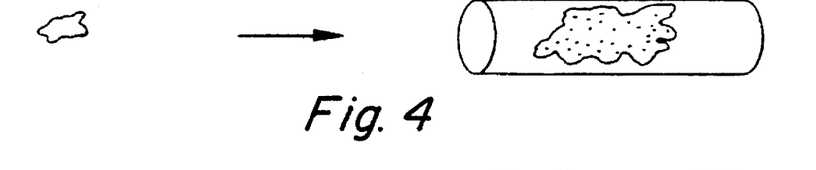
FIG. 4 shows a large patch of sprayed on polymer material before and after deployment.
Figure 5:
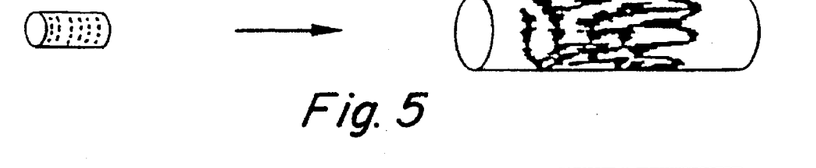
FIG. 5 shows a porous tubular form geometry before and after deployment.
Figure 8:
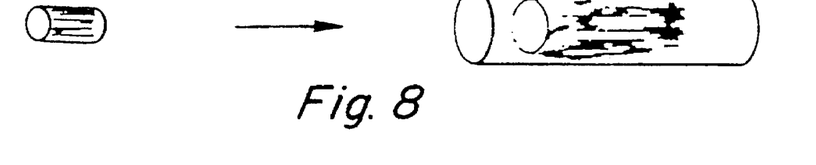
FIG. 8 shows an arcuate (radial, arc) patch geometry of the PEPS polymer before and after deployment.

Additional geometries could include a linear feathered polymer strip applied to a particular area of the vessel wall as shown in FIG. 3. FIG. 4 shows a large patch of polymer which can be sprayed on using a variety of known techniques. Another form of the PEPS application to be utilized in instances, e.g., where structural stability need be imparted to the vessel would be the porous tubular form shown in FIG. 5. Other types of PEPS applications which would impart structural stability to the vessel would be the spiral form application shown in FIG. 7, or the arcuate (radial, arc) patch as shown in FIG. 8.

Conversely, in cases where the severely denuded lesions have irregular surfaces with less fibromuscular components the PEPS process can be used to provide only a thin polymer film to act as a bandage.

The PEPS process is significantly different and is conceptually an advance beyond stents and stenting in achieving vessel patency. Stents have been designed with the underlying primary function of providing a relatively stiff structural support to resist post-PTCA vessel reclosure caused by the vessel's spring-like characteristics. It has been increasingly demonstrated that cellular and biochemical mechanisms as opposed to physical "spring-like" coils, are of a much greater significance in preventing vessel reclosure and PEPS addresses these mechanisms.

The specific object and features of the PEPS process are best understood by way of illustration with reference to the following examples.

Figure 13:
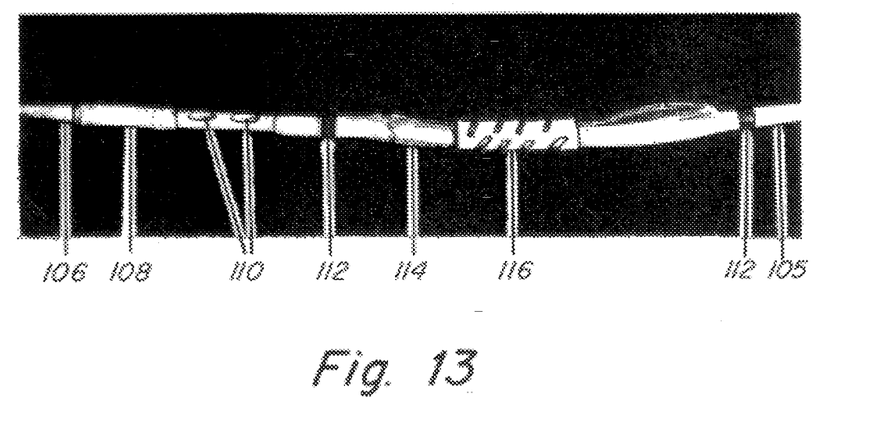
FIG. 13 shows an example of a typical polymer paving catheter with a distal occluding balloon, heating ports, a dilating thermoforming balloon and radiopaque markers. A pre-deployed polymer tube is in place over the thermoforming balloon.

The invention may be readily understood through a description of an experiment performed in vitro using a mock blood vessel made from transparent plastic tubing using a heat-balloon type deployment catheter reference to FIG. 13.

FIG. 13 shows a paving catheter having a tubular shaft 105 which, at its distal end, includes a distal tip 106, a distal occlusion balloon 108, a pair of exit ports 110, radiopaque markers 112, a paving balloon 114, and a polymer tube 116 to be paved onto the interior of a tubular lumen. The distal occlusion balloon 108 is used to occlude the distal end of a treatment site during the paving process. The exit ports 110 are used to inject a heated saline solution into the treatment site to heat the polymer material 116 and render it fluent for paving. The paving balloon 114 is used to mold the fluent polymeric tube 116 into contact with the lumen surface, and the markers 112 are used to provide visualization of the distal end of the device using fluoroscopic methods. It is noted that the catheter device of FIG. 13 is merely one of a wide variety of devices that may be used in the PEPS process, and that the procedure is not intended to be limited strictly to the use of that device.

EXAMPLE 1

A polycaprolactone polymer tube was placed in a low profile condition surrounding a balloon at the distal end of a delivery catheter. The delivery catheter (FIG. 13) with the polycaprolactone tube was then inserted, occlusion balloon end first, into the vessel and manipulated into position at the area of the vessel to be treated.

The distal occlusion balloon on the end of the occlusion catheter was inflated to create a stagnant column of "blood" in the vessel around the balloon delivery catheter and polycaprolactone tube. Saline solution at about 60–80° C. was injected into the area surrounding the delivery catheter, paving balloon and polycaprolactone tube. Once the polycaprolactone tube became fluent, the delivery catheter balloon was inflated to direct the flow of the fluent polycaprolactone and "thermoform" it against the interior wall.

Figure 9:
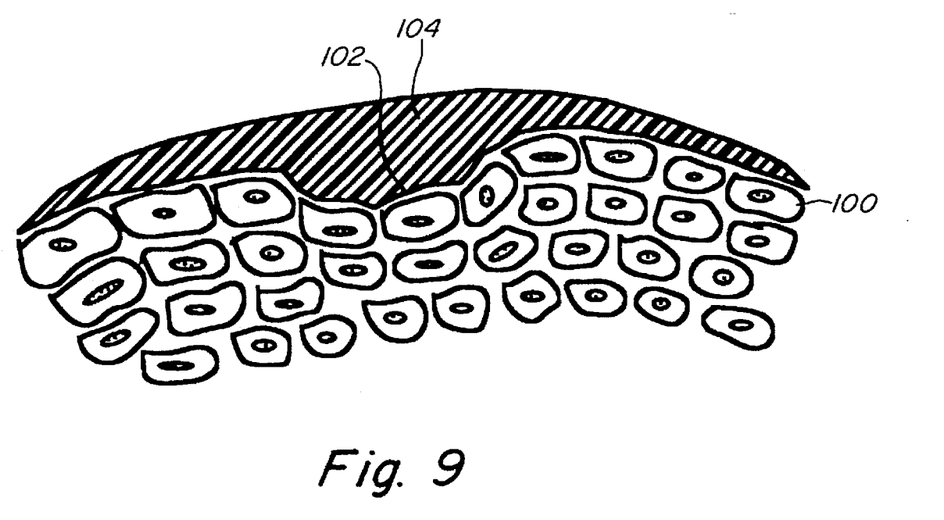
FIG. 9 shows the deployed polymer paving layer in intimate contact applied to a tissue surface.

The polycaprolactone conformed to the inner surface of the vessel, flowing into and filling in surface irregularities, thereby creating a "tailored" fit. As shown in FIG. 9 the tissue surface 100 having a micro-indentation 102 is paved with polycaprolactone 104 in a manner which coats the surface and fills and conforms to the indention. Further, the deployed interior surface of the PEPS polymer was smooth providing an increased vessel (lumen) cross-section diameter and a rheologically advantageous surface with improved blood flow. Upon cessation of heating the polymer rapidly recrystallized providing a paved surface on the vessel wall interior.

The deployment catheter paving balloon was then deflated leaving the polycaprolactone layer in place. The distal occlusion balloon was then deflated and blood flow was allowed to return to normal. The deployment catheter then was removed leaving the recrystallized polycaprolactone layer in place within the vessel.

When performed in a living organism, it is expected that over the course of time, the polycaprolactone seal will become covered with a proteinaceous biologic thin film coat. Depending upon the exact seal chemical composition, the polymer will then biodegrade at a predetermined rate, and "dissolve" into the bloodstream or be absorbed into the vessel wall. While in intimate contact with the vessel wall, pharmacological agents if embedded or absorbed in the polycaprolactone will have a "downstream" effect if released slowly into the bloodstream or may have a local effect on the blood vessel wall, thereby facilitating healing of the angioplasty site, controlling or reducing exuberant media smooth muscle cell proliferation, promoting effective lesion endothelialization and reducing lesion thrombogenicity.

EXAMPLE 2

Figure 10A:
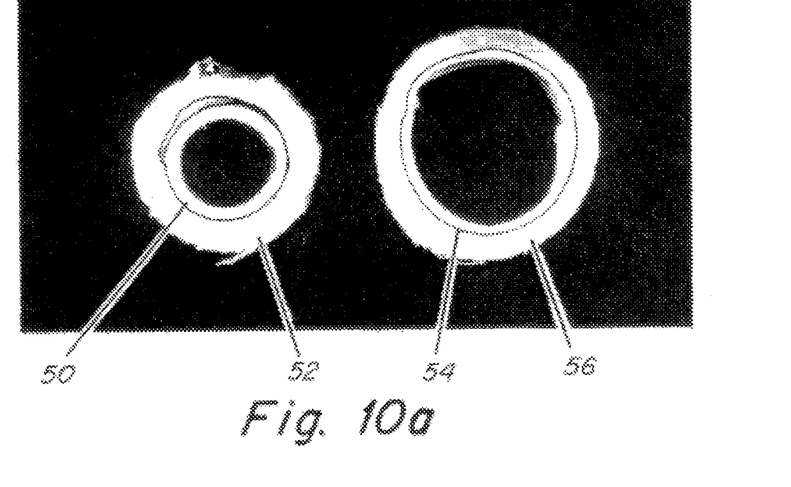
FIG. 10a shows a pre-deployed polymer tube inside of an artery and a post-deployed, i.e., applied, polymer layer, subsequently applied to the same vessel.
Figure 10B:
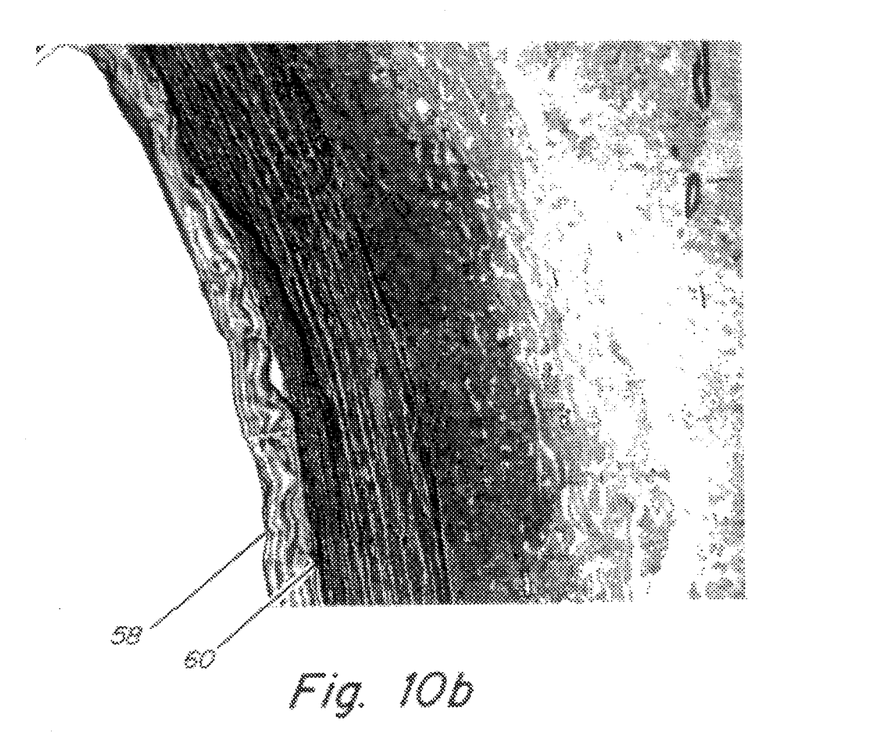
FIG. 10b shows the applied polymer paving layer under light microscopic magnification applied to the endoluminal surface of the vessel.

Polycaprolactone in an initial macroporous tubular configuration was placed in a low profile form in bovine coronary arteries and canine carotid arteries. In the process of deployment the vessels were purposely over extended and sealed through thermal and mechanical deformation of the polymer. In FIG. 10a the pre-deployed polymer tube 50, placed within a baseline vessel 52 may be seen. Following paving, the polymer is locally reconfigured forming an intimate coating 54 which lines the endoluminal surface of the vessel 56. FIG. 10b, a histologic section of a paved artery shows the adherent paving polymer layer in intimate contact with the arterial intimal surface 60.

All polymer sealed vessels remained dilated with a thin layer of macroporous polymer providing a new barrier surface between the vessel lumen and the vessel wall constituents. The unsealed portion of the vessels did not remain dilated.

EXAMPLE 3

Figure 11A:
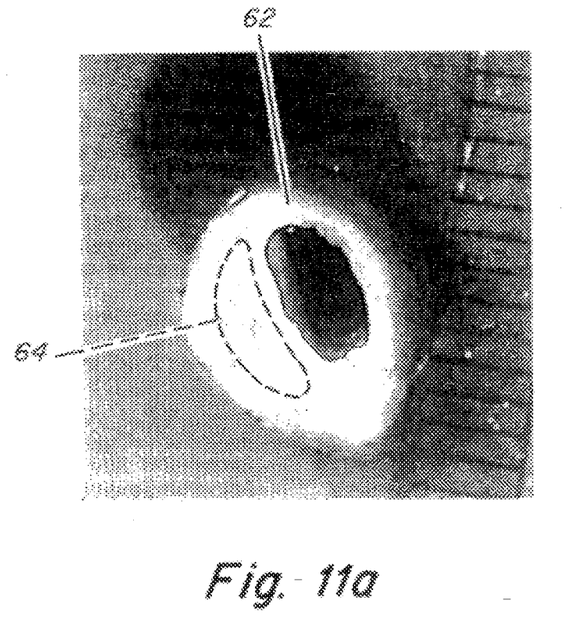
FIGS. 11a and 11b show a human atherosclerotic cartoid artery with a lumen obstructing plaque and the same vessel following paving with a dilated polymer lined lumen.
Figure 11B:
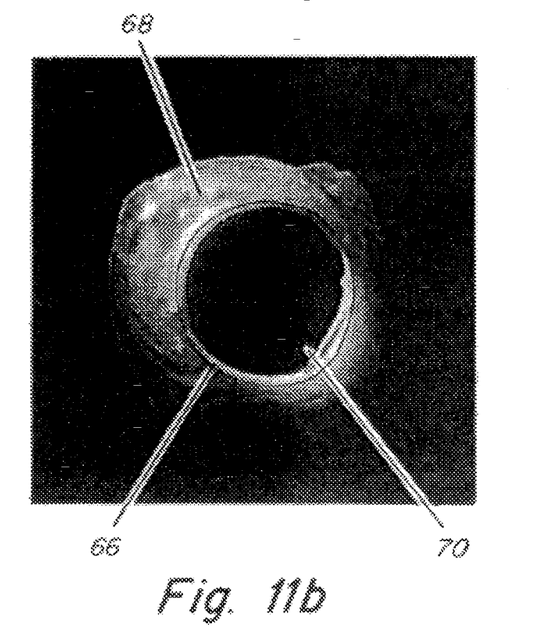

Polycaprolactone paving materials, both in tube and rolled sheet form were placed ex vivo within the lumen of disease compromised atherosclerotic human carotid and coronary arteries. As shown in FIGS. 11a and 11b, following paving the partially obstructed narrowed carotid artery, with an eccentric atheroma 64 (FIG. 11a) was successfully paved with an intimate polymeric liner layer 66 providing a smooth endoluminal surface. The liner layer effectively partitioned the atheroma and supported the diseased arterial wall 68 yielding a patent dilated artery with a large lumen 70 (FIG. 11b).

EXAMPLE 4

Figure 12A:
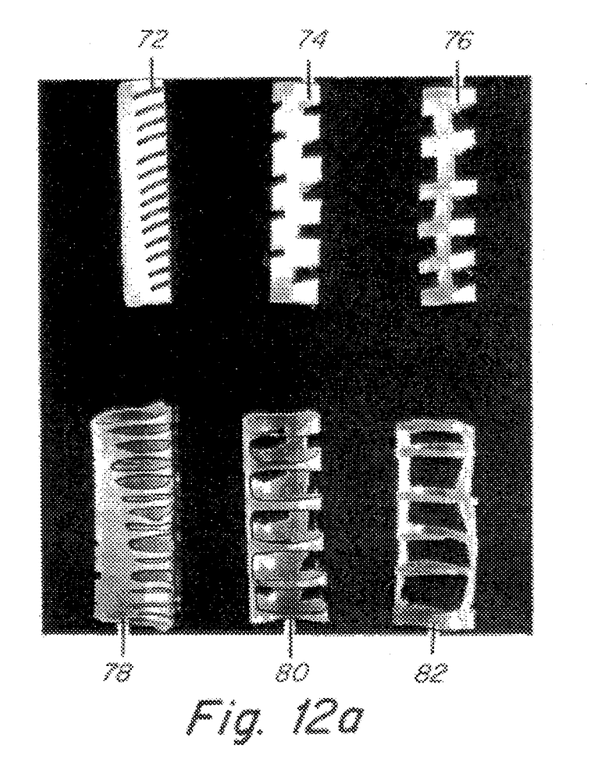
FIG. 12a shows three examples of pre-deployed polymer tubes and their corresponding post-deployed appearance.
Figure 12B:
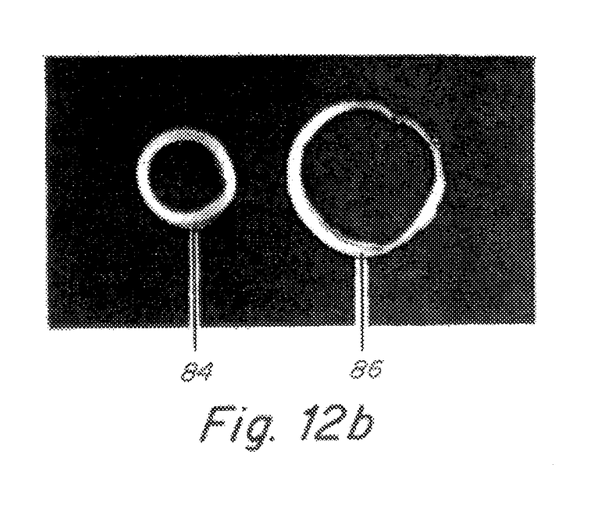
FIG. 12b shows a pre-deployed tube in cross-section and a corresponding post-deployment cross-section.

This example demonstrates some of the variety of post-deployment configurations that may be achieved depending upon the initial processing of the pre-deployed tube. In FIG. 12a, slits or perforations yielding 10%, 30%, or 50% (72, 74, 76, respectively) open surface areas were generated. Following paving in a normal vessel they yielded the corresponding post-deployment polymer layers, i.e., 78, 80 and 82 respectively. FIG. 12b shows an end on cross-sectional view of the predeployed 84 and postdeployed 86 polymer, with wall thinning secondary to local thermoforming being evident. Note a postdeployed tube such as 82 forms an open scaffoled capable of acting as a support, whereas a more dense paving layer 78 yields a more continuous layer capable of providing increased surface contact as in the case in which it is desired to fashion a local drug delivery depot.

These examples demonstrate that the PEPS process may, if desired, provide polymer application with a relatively large degree of surface area coverage and an effective polymer barrier shield. As such, the polymer barrier shield may, if desired, impart sufficient structural stability to maintain a selected vessel diameter. The selected final vessel diameter at which a vessel is sealed is dictated by the particular physiological variables and therapeutic goals which confront the PEPS user.

The geometry of the pre- and post-PEPS application sites may be readily varied. PEPS may be used to merely coat an existing vessel or organ geometry. Alternatively, the PEPS process may be used to impart structural stability to a vessel or organ the geometry of which has been altered prior to the PEPS application. In addition, the PEPS process may itself alter the geometry of the vessel or organ. With reference to FIG. 10a this latter process was used to expand the vessel 52.

A specific and important attribute of the PEPS technique and the polymers which are employed is the significantly lower degree of compliance mismatch or similarities of stiffness (inverse of compliance) between the vessel and the polymer seal as compared to metal stents. The vessel damage from compliance mismatch discussed above may be eliminated by the PEPS process utilizing a variety of available polymers. Additionally, compliance mismatch greatly modifies the characteristics of fluid wave transmission along the vessel with resultant change in local flow properties, development of regional change in shear forces and a subsequent vessel wall hypertrophy which acts to reduce vessel cross-sectional area and reduces blood flow. Further, the substructural reduction of compliance mismatch of the PEPS technique at first minimizes and then, upon dissolution eliminates local flow abnormalities and up and downstream transition zone hypertrophy associated with metal stenting.

PEPS has the flexibility of being safely and effectively used prophylactically at the time of initial PTCA in selected patients or being incorporated as part of the original dilation procedure as a second stage prophylactic vessel surface "finishing" process. For example, the invasive cardiologist may apply the PEPS technique on a wide clinical basis after the first episodes of restenosis. In addition, because the PEPS technique significantly aids in the vascular healing process post intervention, it may be readily used prophylactically after initial angioplasty prior to any incidence of restenosis. This would free the patient from the risks of repeat intracoronary procedure as well as those associated with metal stenting.

Equivalents

Although specific features of the invention are shown in some drawings and not in others, it is for convenience only as each feature may be combined with any or all of the other features in accordance with the invention. It should be understood, however, that the foregoing description of the invention is intended merely to be illustrative thereof by way of example, and that other modifications, embodiments, and equivalents may be apparent to those skilled in the art without departing from its spirit. It will be understood by those of ordinary skill in the art that variations such as the use of polymers other than those described can be substituted or added consistent with this invention.

Having thus described the invention, what we desire to claim and secure by Letters Patent is:

1. A method for forming a biocompatible polymer coating on a tissue surface of a lumen in a body vessel or hollow organ which comprises the steps of:
   a) providing a biocompatible polymeric material which is non-fluent at body temperature and which is fluent at an elevated temperature;
   b) heating the material to render the polymer fluent;
   c) contacting the fluent polymer with a surface to be coated; and
   d) allowing the fluent polymer to cool into a non-fluent biocompatible polymeric coating on the surface.

2. A method as in claim 1 wherein the polymeric coating is biodegradable.

3. A method as in claim 2 wherein the biodegradable polymeric coating further includes a therapeutic agent.

4. A method as in claim 3 wherein the therapeutic agent is selected from the group consisting of anti-thrombotic agents, thrombolytic agents, vasodilating agents, anti-proliferative agents, intercalating agents, growth modulating factors, monoclonal antibodies, anti-inflammatory agents, lipid and cholesterol sequestrants, antisense oligonucleotides, ribozymes, aptomers and combinations thereof.

5. A method as in claim 1 wherein the biocompatible polymer is selected from the group consisting of polymers and copolymers of hydroxycarboxylic acids, polyurethanes, polyesters, polyamides, polyacrylonitriles, polyphosphazenes, polylactones, polyanhydrides, polyethylenes, polyalkysulfones, polycarbonates, polyhydroxybutyrates, polyhydroxyvalerates, hydrocarbon polymers, polypropylenes polyvinylchlorides, ethylene vinyl acetates and combinations thereof.

6. A method as in claim 1 wherein the polymeric coating has a thickness in the range of approximately 0.001–1.0 mm.

7. A method as in claim 1 wherein the tissue surface comprises a lumen in a body vessel.

8. A method as in claim 1 wherein the body vessel comprises a blood vessel.

9. A method as in claim 1 wherein the coating comprises a substantially continuous layer.

10. A method as in claim 9 wherein the continuous layer includes perforations.

11. A method as in claim 1 wherein the coating comprises a plurality of isolated coating domains, the domains comprising stellate, amorphous or spot geometries.

12. A method as in claim 1 wherein the coating portion opposite the tissue contacting surface is substantially smooth.

13. A method for forming a biocompatible polymer coating on a tissue surface of a lumen in a body vessel or a hollow organ which comprises the steps of:

a) providing a biocompatible polymeric material having a variable degree of fluency in response to a stimulus;

b) providing the stimulus to the material to render the polymer fluent;

c) contacting the fluent polymer with a surface to be coated; and d) allowing the fluent polymer to return to a non-fluent state, thereby providing a biocompatible polymeric coating on the surface.

14. A method as in claim 13, wherein the polymeric coating is biodegradable.

15. A method as in claim 13, wherein the biodegradable polymeric coating further includes a therapeutic agent.

16. A method as in claim 13 wherein the body vessel comprises a blood vessel.

17. A method for forming a biocompatible polymer coating on a tissue surface which comprises the steps of:

a) providing a biocompatible polymeric material which is non-fluent at body temperature and which is fluent at an elevated temperature;

b) heating the material to render the polymer fluent;

c) contacting the fluent polymer with a surface to be coated; and d) allowing the fluent polymer to cool into a non-fluent biocompatible polymeric coating on the surface, the coating defining a passageway open to fluid flow.

18. A method as in claim 17 wherein the polymeric coating is biodegradable.

19. A method as in claim 17 wherein the biodegradable polymeric coating further includes a therapeutic agent.

20. A method as in claim 17 wherein the tissue surface comprises a lumen in a body vessel or hollow organ.

21. A method as in claim 17 wherein the body vessel comprises a blood vessel.

* * * * *